US00PP14616P29

(12) United States Plant Patent
Villa

(10) Patent No.: US PP14,616 P2
(45) Date of Patent: Mar. 16, 2004

(54) YUCCA PLANT NAMED 'MONCA'

(50) Latin Name: *Yucca recurvifolia*
Varietal Denomination: Monca

(75) Inventor: Gerardo L. Villa, Azusa, CA (US)

(73) Assignee: Monrovia Nursery Company, Azusa, CA (US)

( * ) Notice: Subject to any disclaimer, the term of this patent is extended or adjusted under 35 U.S.C. 154(b) by 47 days.

(21) Appl. No.: 10/264,199

(22) Filed: Oct. 3, 2002

(51) Int. Cl.[7] ..... A01H 5/00
(52) U.S. Cl. ..... Plt./373
(58) Field of Search ..... Plt./373, 372, 313, Plt./395

(56) References Cited

PUBLICATIONS http://members.tripod.com/~Hatch_L/yucca.html, Laurence C. Hatch, Feb. 2002, pp. 1–8, 'Yucca Page', see esp. p. 6.*

* cited by examiner

*Primary Examiner*—Anne Marie Grunberg
(74) *Attorney, Agent, or Firm*—C. A. Whealy

(57) ABSTRACT

A distinct cultivar of Yucca plant named 'Monca', characterized by its compact, upright and outwardly arching growth habit; long narrow sword-like leaves; and dark and light green variegated leaves.

1 Drawing Sheet

Botanical classification/cultivar designation: *Yucca recurvifolia* cultivar Monca.

BACKGROUND OF THE INVENTION

The present invention relates to a new and distinct cultivar of Yucca plant, botanically known as *Yucca recurvifolia*, and hereinafter referred to by the cultivar name Monca.

The new cultivar was discovered by the Inventor in a controlled environment in Azusa, Calif. as a naturally-occurring whole plant mutation of an unidentified selection of *Yucca recurvifolia*, not patented. The new Yucca was observed as a single plant in a group of plants of the unidentified selection of *Yucca recurvifolia* on Oct. 13, 1999. The selection of this plant was selected on its unique leaf variegation pattern.

Asexual propagation of the new cultivar by tissue culture propagation at Azusa, Calif. since Oct. 13, 1999, has shown that the unique features of this new Yucca plant are stable and reproduced true to type in successive generations of asexual propagation.

The new Yucca has not been observed under all possible environmental conditions. The phenotype may vary somewhat with variations in environment such as temperature and light intensity, without, however, any variance in genotype.

SUMMARY OF THE INVENTION

The following traits have been repeatedly observed and are determined to be the unique characteristics of 'Monca'. These characteristics in combination distinguish 'Monca' as a new and distinct cultivar:

1. Compact, upright and outwardly arching growth habit.
2. Long narrow sword-like leaves.
3. Dark and light green variegated leaves.

Plants of the new Yucca differ from plants of the parent selection in the following characteristics:

1. Plants of the new Yucca are more compact than plants of the parent selection.
2. Leaves of plants of the new Yucca are shorter, narrower and more recurved than leaves of plants of the parent selection.
3. Leaves of plants of the new Yucca are variegated whereas leaves of plants of the parent selection are not variegated.

The new Yucca can be compared to plants of the *Yucca filamentosa* cultivar Golden Sword, not patented. However in side-by-side comparisons conducted in Azusa, Calif., plants of the new Yucca differed from plants of the cultivar Golden Sword in the following characteristics:

1. Leaves of plants of the new Yucca were broader than leaves of plants of the cultivar Golden Sword.
2. Variegation pattern of leaves of plants of the new Yucca was less distinct than variegation pattern of leaves of plants of the cultivar Golden Sword.
3. Plants of the new Yucca were not as cold temperature tolerant as plants of the cultivar Golden Sword.

DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new Yucca. The photograph comprises a side perspective view of a typical potted plant of 'Monca'.

DETAILED BOTANICAL DESCRIPTION

The aforementioned photographs and following observations and measurements describe plants grown in Azusa, Calif. in an outdoor nursery with day temperatures ranging from 22 to 35° C. and night temperatures ranging from 9 to 16° C. Plants used for the photograph and the description were about 3.5 years old and were grown in 7-gallon containers. In the description, color references are made to The Royal Horticultural Society Colour Chart, 1995 Edition, except where general terms of ordinary dictionary significance are used.

Botanical classification: *Yucca recurvifolia* cultivar Monca.

Parentage: Naturally-occurring whole plant mutation of an unidentified selection of *Yucca recurvifolia,* not patented.

Propagation:

*Method.*—By tissue culture.

*Time to initiate roots on a micro propagated cutting.*—About 21 days at 21° C.

*Time to produce a rooted micro propagated plant.*—About 210 days at 18° C.

*Root description.*—Fine, fleshy, and fibrous.

Plant description:

*Plant shape.*—Compact, upright and outwardly arching; leaves recurved.

*Plant height.*—About 60 cm from soil level to top of leaf plane.

*Plant diameter or spread.*—About 69 cm.

*Growth rate.*—Relatively slow.

*Stem description.*—Diameter, at base: About 4.5 cm. Internode length: About 1 cm. Aspect: Upright. Strength: Strong. Texture: Woody; smooth, glabrous. Color: More gray than 177B.

*Foliage description.*—Arrangement: In spiral whorls, rosette; simple. Leaves sessile and clasping. Orientation: Initially upright, then recurved. Shape: Linear, sword-like. Apex: Acuminate with short spines at tips; spines about 5 to 7 mm in length. Margin: Entire. Base: Attenuate. Texture: Upper surface: Smooth, glabrous. Lower surface: Coarse, glabrous. Venation pattern: Parallel. Length: About 37 cm. Width: About 2.8 cm. Color: Longitudinally variegated. Young leaves, upper surface: 144B to 144C. Young leaves, lower surface: 146D. Fully expanded leaves, upper surface: Margins and longitudinal stripes, 147A to 147B; centers, more gray than 153A; centers with development, closer to 153C. Fully expanded leaves, lower surface: 153A. Venation, upper and lower surfaces: 153A.

Flower description: Flowers have not been observed on plants of the new Yucca.

Disease/pest resistance: Under commercial conditions, resistance to pathogens and pests common to Yuccas has not been observed.

Temperature tolerance: Plants of the new Yucca have been observed to tolerate temperatures from −17 to 49° C.

It is claimed:

1. A new and distinct cultivar of Yucca plant named 'Monca' as illustrated and described.

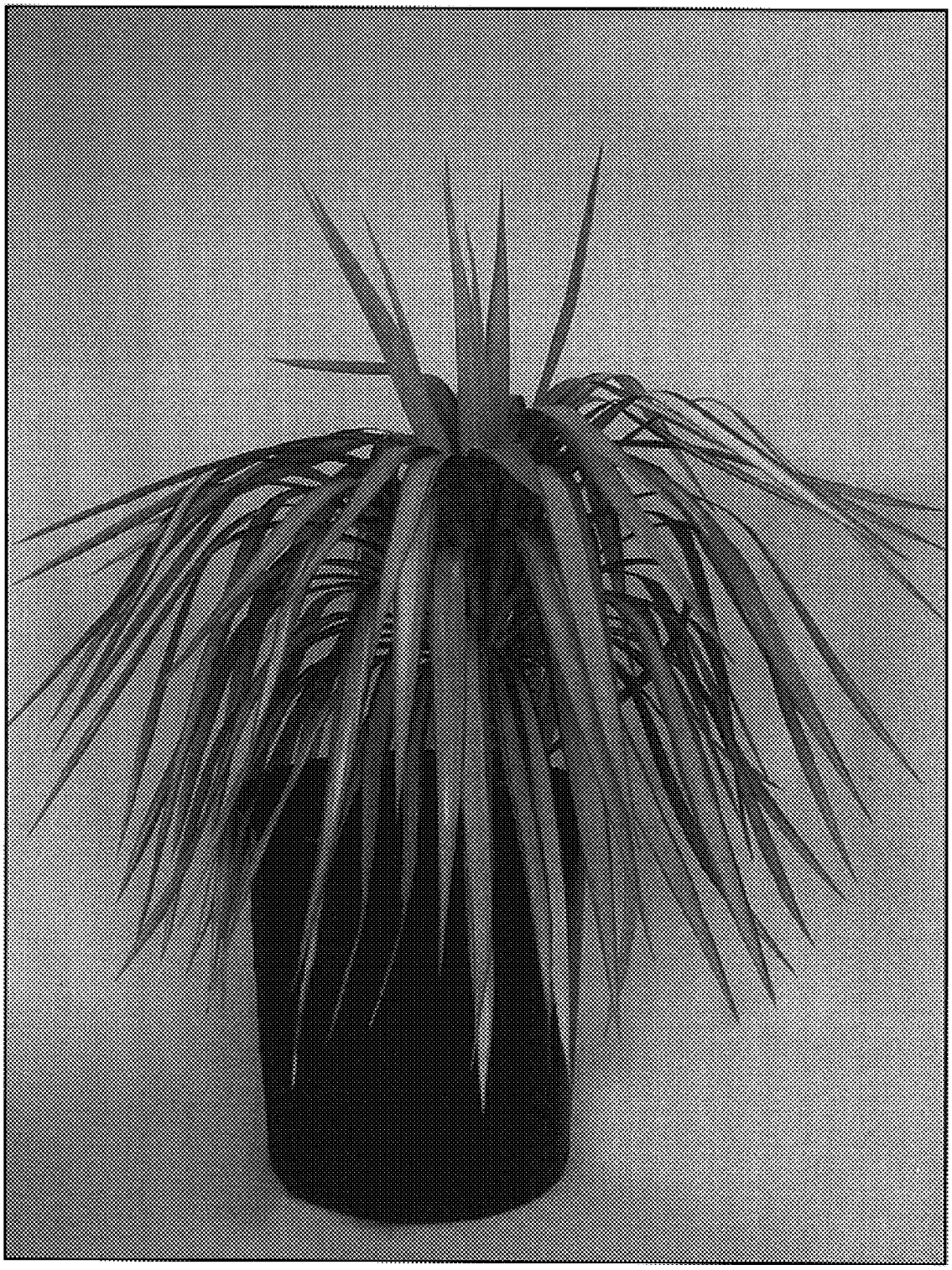

* * * * *